United States Patent [19]

Hager

[11] Patent Number: 4,857,323

[45] Date of Patent: Aug. 15, 1989

[54] PRESERVATIVE FOR WOOD

[76] Inventor: Bror O. Hager, Forsetevagen 5, Djursholm, Sweden, S-182 63

[21] Appl. No.: 19,655

[22] Filed: Feb. 27, 1987

[30] Foreign Application Priority Data

Feb. 27, 1986 [SE] Sweden .................................. 8600888

[51] Int. Cl.$^4$ ....................... A01N 55/02; A01N 59/14
[52] U.S. Cl. .................................... 424/659; 514/494; 514/500
[58] Field of Search ................. 424/148; 514/494, 500

[56] References Cited

U.S. PATENT DOCUMENTS 4,335,109  6/1982  Hill ...................................... 424/140

FOREIGN PATENT DOCUMENTS 2082912  3/1982  United Kingdom .

OTHER PUBLICATIONS

XX equivalent to Swed. 430,865.

Primary Examiner—Allen J. Robinson
Attorney, Agent, or Firm—Burns, Doane, Swecker & Mathis

[57] ABSTRACT

Preservative solutions for wood and other cellulosic fibrous materials are provided which include zinc acetate and copper acetate in an amount at least about the same as the zinc acetate, and optionally boric acid and/or a basic material.

12 Claims, No Drawings

PRESERVATIVE FOR WOOD

BACKGROUND OF THE INVENTION

The present invention relates to further developments in preservatives for wood and other fibrous materials for protection against decay.

For more than a century, aqueous solutions of copper sulfate and zinc chloride have been used as wood preservatives. While these salt solutions have provided adequate protection against decay, they are, however, prone to certain disadvantages. Copper sulfate tends to attack iron and also, in certain instances, has only a weak preservative affect. Zinc chloride also acts as a corrosive and, in addition, has a lower preservative effect than the copper sulfate. For these and other reasons the aqueous preservative solution based on copper sulfate and zinc chloride have been replaced by other salt-based preservatives in which copper and zinc compounds are present.

SUMMARY OF THE INVENTION

It has been found unexpectedly that a preservative composition comprising copper acetate and zinc acetate provides advantages over prior art preservative compositions. An advantage of the present invention is that preservative compositions based on copper and zinc acetate salts do not result in corrosion of metal, such as iron, which is integral with the preserved organic fibrous material. It is an aspect of the present invention that full cell treatment of the fibrous materials to be preserved can be achieved without resort to the high concentrations to which the art resorted. Accordingly, it is another advantage of the present invention that fixation of the preservatives in the fibrous materials also can be achieved without resort to prior concentrated solutions. It is another advantage that unexpected aspects of the novel preservative aid in transporting the preservative from those parts of the fibrous material which have more fixed preservative to those parts which have a lower fixed concentration of the preservative. Thus, an important feature of the present invention is that a more uniform distribution and a more effective protection of the materials treated is obtained. An additional advantage is that the acetate based preservative of the present invention decomposes with an improved fixation of copper and zinc in the treated material with the formation and subsequent evaporation of free acetic acid.

In summary the present invention provides a preservative composition for organic fibrous materials comprising zinc acetate and at least about 45% by weight of copper acetate based on the total metal acetate present. In various embodiments of the present composition, boric acid may be present. In further embodiments, alkali salts may be present in an amount effective to further inhibit corrosion.

In addition, the present invention provides a process for preserving organic fibrous materials comprising treating an organic fibrous material with an aqueous solution of a preservative comprising zinc acetate and at least 45% by weight of copper acetate based on the total metal acetate present. In various embodiments, the preservative is present in the solution in a concentration of at least 1%.

DETAILED DESCRIPTION OF THE PREFERRED EMBODIMENTS

The present invention is directed to a process and a preservative composition for preserving wood and similar organic fibrous materials, such as paper, wood chips and fibers, pulp and the like. The prior art has resorted to aqueous solutions of copper sulfate and zinc chloride which, in spite of their solubility, have given good preservative protection. For any preservative in this aspect, it is important that the preservative ingredients, that is copper and zinc, be fixed in the material preserved. Accordingly, the copper and zinc salts used as preserving agents must be sufficiently soluble to allow their penetration into the treated material and the preservative ingredients must then be fixed such that they do not leach or elute when the material is exposed to water.

In this regard, comparative leaching tests have been carried out, the results of which are shown in Table 1. In these tests, blocks of pine sap wood with a volume of 15 cubic centimeters were full cell impregnated with different strong solutions of copper sulfate and zinc chloride. After drying, the blocks were leached in running tap water for thirty days, whereafter the remaining amounts of copper or zinc were determined.

TABLE 1

| Original impregnating percent Cu or Zn in solution of copper sulphate or zinc chloride | Percent Cu or Zn remaining after leaching of Cu or Zn, based on original impregnating solution | | | |
|---|---|---|---|---|
| | Cu | Fixation Value* | Zn | Fixation Value* |
| 0.1 | 58 | 0.058 | 45 | 0.045 |
| 0.2 | 49 | 0.098 | 33 | 0.066 |
| 0.3 | 42 | 0.126 | 27 | 0.081 |
| 0.4 | 36 | 0.144 | 24 | 0.096 |
| 0.5 | 32 | 0.160 | 19 | 0.095 |
| 0.7 | 27 | 0.189 | 14 | 0.098 |
| 1.0 | 21 | 0.210 | 10 | 0.100 |
| 1.2 | 19 | 0.228 | 9 | 0.108 |

*The "fixation value" is obtained by multiplying the percent Cu or Zn in solution by the percent remaining after leaching.

Regarding the original impregnating solutions in Table 1, an amount of 0.1% corresponds to 0.393% of $CuSO_4.5\ H_2O$ (=0.1% Cu) or corresponds to 0.208% $ZnCl_2$ (=0.1% Zn).

It has been found unexpectedly that as the sulfates and chlorides are replaced by the copper and zinc acetates, an improved fixation of the preserving ingredients copper and zinc is attained. Moreover, it has been found unexpectedly that similar or even better fixation can be obtained using a lower concentration of the copper or zinc acetates. However, the resulting fixation is more improved for copper than for zinc. For example, copper acetate solutions containing 0.3% copper have been found to result in about twice the amount of copper fixed than when solutions containing the same amount of copper as copper sulfate are used.

Similarly, by the use of zinc acetate instead of zinc chloride, a correspondingly improved fixation is achieved. While the zinc compounds are not fixed to the same degree as copper compounds, by the use of a low concentration of zinc acetate instead of zinc chloride, correspondingly improved zinc fixation values are attained. However, it appears that the improvement in the zinc fixation by the use of zinc acetate instead of zinc chloride is only about half as good as that achieved for copper by the use of copper acetate instead of copper sulfate.

It has also surprisingly been found that the fixation value of copper decreases with an increase in the copper acetate in solution. For example, after impregnation with an acetate solution containing 0.3% copper, the copper is fixed to about 85%; for a solution containing about 0.6% copper, the fixation value is about 64%; an if the solution contains about 1.0% copper only about 48% of the copper is fixed. On the other hand it can be observed that the amount of zinc which can fixed is surprisingly invariable within a wide concentration range. As seen in Table 1 concerning the leaching results for using zinc chloride, it is evident that the amount of zinc remaining after leaching increases with the amount of zinc chloride up to a zinc content of about 0.3 to 0.4% (this is determined by multiplying the percent of Zn remaining by the percent of Zn in the zinc chloride solution). Thereafter, the degree to which fixation decreases is about the same as that by which the concentration of zinc increases in the impregnating solution. As seen by Table 1, when the initial solution has 0.3% zinc, 27% of the initial zinc is fixed, while when the impregnating solution has 1.2% zinc, only 9% of the zinc is fixed. Moreover, even when the initial concentration of zinc is increased by 400%, at 0.3% zinc in the initial solution the fixation value is 0.081, while for a 1.2% concentration in the initial solution the fixation value is increased to only 0.108. It is thus seen that a four-fold increase in the initial zinc concentration only provides a 33% increase in the fixation value. Similarly, if the initial concentration is increased three-fold, that is from 0.4% to 1.2% the protecting amount of zinc which is fixed increases by only 12% from 0.096 to 0.108. Accordingly, there would not seem to be much reason to use solutions of zinc chloride containing over 0.3 to 0.4% zinc. Nevertheless, it has been found unexpectedly that the fixation of the zinc is considerably increased when the acetate salt is used instead of the chloride salt.

The amount of preservative for amount of wood as given above is in the form of a concentration of a solution which has been introduced into the wood by a full cell treatment. By the "full cell" treatment, the wood is exposed to a vacuum before the solution is introduced under pressure into the wood. This treatment gives the highest possible retention of solution in the wood, in that not only the walls of the cells in the wood are saturated with solution but also that the cells are filled with solution. To use full cell treatment when carrying out experiments is common and well known in the art, and it is employed because it gives a uniform distribution of the preservative. However, such a uniform distribution in the preserved material is not readily possible if more concentrated solutions are used, by which treating methods a lesser amount of the preserving ingredient is impregnated and fixed.

The fixation of the preservative has a close connection with the amount of preservative introduced for weight of wood. It is easier to fix preservatives which are provided in a lesser concentration than those which are provided in higher amounts. Accordingly, the aspect of the present invention by which a less concentrated solution can be used provides an advantage over the prior art preservative compositions, which as a rule require higher concentrations and therefore are not as readily fixed in the preserved material.

It has also been unexpectedly observed that excess preservative present in treated areas of the material will diffuse to those parts of the treated material which have a lower concentration of the fixed preservative agents. This is a common situation because in practical aspects the outer parts of the preserved material, such as lumber parts, will always be presented with more preservatives at their exposed surfaces. Accordingly, the inner parts of the treated material will have less preservative fixed therein. The properties of the present preservative aid to transport the preservative from that area of the material which has a higher concentration to that area which has a lower concentration. Moreover, the internal area of the treated material which initially has a lower concentration of fixed preservative is more often subject to attack by agents tending to destroy the wood. In this way, a more uniform distribution and a more effective protection of the treated material is achieved.

It is an additional advantage that the acetates of the present invention have a tendency in the long run to decompose with a subsequent forming or evaporation of free acetic acid and thus a proceeding improved fixation of the preservative agent.

It is generally known that copper salts give an excellent decay protection. However, there are certain fungi which are resistant to copper and which can quickly destroy the wood and give incalculable and troublesome damages. Zinc has also been indicated as a preservative agent, although in general copper has about four times as high a preservative effect as does zinc. Nevertheless, zinc has a more rounded or systemic effect and in particular cases, such as when copper alone is not as effective as would be supposed, the combination of zinc and copper provides a synergistic preservative effect. Because zinc compounds are not as readily fixed as copper compounds, it is preferred that they be used only in limited amounts, thereby avoiding decreasing the effect of the copper present or decreasing the fixation of the copper preservative agent.

In this regard, laboratory investigations suggest that the preservative action against copper resistant fungi appears to be sufficient if the zinc acetate reaches 10 to 15% of the total amount of the metal acetate in the preservative. However, in these investigations, no leaching experiments were carried out. Therefore, because zinc has a lower leaching resistance than copper does, as shown in Table 1 the zinc content may be increased to 25%, and preferably up to about 55%. Additionally, the best overall preservative results are obtained when the copper acetate content is high. Therefore the zinc acetate should be present only to a limited amount. In general, the content of copper acetate should be at least about 45 to 50%, preferably over 60%, and most preferably over 75% of the total amount of the metal acetate present. It is also preferred that the copper acetate not exceed 90% of the total metal acetate present, as in such cases the effect of the zinc will be less than desired. This is in stark contrast to commonly used preservative agents in which copper and zinc salts have been based on a higher amount of zinc and a lower amount of copper. For example, a well known preservative agent, chromated copperized zinc chloride, contains the preservative agents zinc chloride and copper chloride which are present in a ratio of zinc to copper of about 10 to 1. Similarly as described in Swedish Patent No. 430,865 (corresponding to U.S. patent appln. Ser. No. 185,539, filed Sept. 9, 1980, now abandoned, the disclosure of which application is herein incorporated by reference), zinc and copper salts are used in which the zinc salt is present in an amount about 5 times as high as the amount of copper salt.

In another embodiment of the present invention, boric acid, $H_3BO_3$, may be included in the preservative composition. The boric acid can hasten the decomposition of the acetates and support the fixation of the metal radicals. Further, the boric acid contributes to protect the wood or other fibrous material against mold and blue stain during drying after impregnation. It is preferred that the boric acid not be present in great amounts, as a high concentration of boric acid can reduce leaching resistance of the metal radicals. Additionally, boron compounds, while they may have some preservative effect, are not effectively fixed and are readily leached. It is preferred that the boric acid be present in an amount of up to about 10% by weight, most preferably about 5% to 10% based on the metal acetates present.

As mentioned above, an unexpected advantage of the present invention is that the use of copper and zinc acetates can avoid corrosion against iron. Additionally corrosion can be reduced if the impregnating solutions are not substantially acidic. Accordingly, small amounts of ammonia or ammonium or alkali salts can be used in the present invention. For example, it has been found that up to about 0.1% of sodium nitrite or ammonium acetate, based on the preservative solution, provides very effective resistance to corrosion. Other alkaline salts include hydroxides, such as of sodium or potassium, and nitrites, such as potassium or ammonium. A preferred alkali material includes sodium, potassium, or ammonium nitrite alone or in combination with ammonium acetate, such that the total amount of the alkali material is up to about 0.1% based on the total preservative solution.

It has been known to use copper acetate as a preservative agent and such has been tested in the field for many years. While a good average durability of wood has been achieved in these tests, occasional decay damages have occurred which cannot be tolerated. In addition, combinations of copper preservatives, either alone or with boric acid, have been used. Again, however, the preservative results were not as good as expected and it was clear from the results that the boric acid had no real preservative effect.

EXAMPLE

The following example describes the preservative effect of the present composition, which has been extensively investigated in field tests. These tests were carried out for about five years.

By the process of the present invention, a composition comprising 73% by weight copper acetate, 23% by weight of zinc acetate, and 4% by weight of boric acid was dissolved in water to provide aqueous solutions containing 0.7, 0.9, 1.3, 1.8, and 2.6% of this preservative. For each of the various concentrations, 20 pine wood stakes were impregnated and, after storing and drying, were placed in the ground in a field to half their height.

As a comparison, other stakes were treated with a solution of 1.8% of the preservative K33 which contains copper, chromium and arsenic compounds (see Swedish Pat. No. 139,177, which is herein incorporated by reference). The K33 preservative is used in about 60 countries and is considered to be the most effective preservative which is readily obtainable.

Also placed in each field were untreated stakes, as a comparison against each of the preserved stakes.

Each year all stakes in the field were inspected and the extent of their decayed condition was calculated and given in the form of "decay index". If no damage at all can be observed on any stake, the decay index is 0. However, if all stakes are quite decayed, the decay index is given as 100.

The tests were carried out in two fields, one being at Simlangdalen, Sweden, which has extremely adverse decay conditions, and the other at Tastrup, Denmark which has more normal conditions. The stakes were inspected over a five year period during which the following results were obtained:

TABLE 2

| Preservative | Concentration of solution | Decay index Simlangdalen | Tastrup |
|---|---|---|---|
| CZB* | 0.7 | 39 | 8 |
|  | 0.9 | 34 | 5 |
|  | 1.3 | 13 | 0 |
|  | 1.8 | 3 | 0 |
|  | 2.6 | 0 | 0 |
| K33 | 1.8 | 6 | 5 |
| Untreated stakes |  | 100 | 100 |

*CZB: 73% copper acetate, 23% zinc acetate, 4% boric acid

It was found that the untreated stakes at Simlangdalen had an average durability of one year while at Tastrup the untreated stakes had an average durability of about 2.9 years.

From Table 2 it is seen that the present composition, when employed in a concentration of about 1.3% to 1.8%, gives the same protection or better preservative protection than a 1.8% solution of K33. In the Tastrup field, a 0.9% concentration of the preservative composition of the present invention provides the same protection as a 1.8% solution of the K33 preservative; and at identical 1.8% concentrations, the present preservative provides much more effective protection than the K33 preservative.

In order to show that the zinc and copper acetates in their proportions have an important effect on the preservation of the treated material, an additional comparison was made using only zinc acetate and boric acid. These tests were done concurrently with those in the described Table 2. These results are shown in Table 3 and were also determined after 5 years of inspection.

TABLE 3

| Preservative | Concentration of solution | Decay index Simlangdalen | Tastrup |
|---|---|---|---|
| ZB* | 1.1 | 89 | 90 |
|  | 1.6 | 79 | 95 |
|  | 2.2 | 78 | 73 |
|  | 3.1 | 36 | 53 |
|  | 4.4 | 19 | 45 |

*Zinc acetate and boric acid

The preservative effect of the CZB composition of the present invention can be seen by comparing Tables 2 and 3 and, as shown, is much higher than for the ZB solution. The results for Simlangdalen show that 0.7 to 0.9% of the CZB solution provides the same preservative protection as 3.1% of the ZB solution. Additionally, it was found that 0.7% of the CZB solution at Tastrup gives far better results than a 4.4% solution of ZB. From this it is clear that the copper acetate/zinc acetate/boric acid composition provides several times the preservative effect as use of only zinc acetate and boric acid. This, in fact, is somewhat expected as zinc has about 4 times less of a preservative effect than copper, as described above, and this effect is further reduced by leaching.

The results shown in Table 2 are quite unexpected. The K33 preservative was developed for almost 40 years and has never since been surpassed. However, by the present invention, it has been discovered that a preservative containing copper acetate and zinc acetate provides much higher preservative effects and which can be used in a lower concentration than in a K33 preservative. An additionally important and distinct environmental advantage is that the present preservative, in contrast to the K33 preservative, does not require chromium or arsenic compounds.

When the present preservative composition is used in a water solution, the concentrations are generally about 1 to 2% when used for ordinary full cell treatment of Swedish pine. As a rule Swedish pine absorbs about 300 liters of solution per cubic meter of wood. For the treatment of wood to be used in sea water where Teredo occurs, as a rule a concentration of about 3 to 4% of the present preservative solution should be used; that is, where the treated wood is to be exposed to sea water, the preservative concentration in the solution is generally doubled. When the Lowry treatment is used a much smaller amount of the preservative solution is used. The Lowry treatment starts without initial vacuum, the solution being directly introduced into the wood by pressure by use of a pressure vessel. Then the solution in the pressure cylinder (or, equivalent pressure vessel) which has not been actually introduced into the wood is removed from the cylinder by a pump, and a vacuum is applied to the interior of the vessel. Part of the solution introduced into the wood is recovered from the wood by means of the compressed air introduced into the wood during the pressure period. Accordingly, for the Lowry treatment a solution containing about 2 to 4% of the preservative composition is preferably employed to give the wood the desired amount of preservative. If a Reuping treatment is desired, the concentration of the preservative is generally about 4–5%.

Various modifications and additions to the described embodiments can be made by those of ordinary skill in the art. Such changes and adaptations are intended to be within the scope and spirit of the present invention as defined by the claims.

I claim:

1. A preservative composition for organic fibrous materials comprising an effective preservative amount of zinc acetate and copper acetate, wherein said composition contains about 50% to about 90% by weight of copper acetate and about 10% to about 35% by weight of zinc acetate, based on the total metal acetate present.

2. A preservative composition as defined by claim 1 wherein the copper acetate is present in an amount of about 60% to about 90%.

3. A preservative composition as defined by claim 1 wherein the copper acetate is present in an amount of about 75% to about 90%.

4. The preservative composition defined by claim 1, further comprising up to 10% by weight of boric acid based on the total metal acetate present.

5. The preservative composition of claim 4 wherein said boric acid is present in an amount of about 5 to 10%.

6. A preservative solution comprising about 1% to about 4% of a preservative composition as defined by claim 1, further comprising up to 0.1% of an alkali material to inhibit corrosion of metals.

7. The preservative solution as defined by claim 6, wherein said alkali compound is selected from the group consisting of ammonia, ammonium salts, nitrite salts and mixtures thereof.

8. The preservative composition as defined by claim 6, wherein said alkali compound is selected from the group consisting of sodium nitrite, ammonium acetate and mixtures thereof.

9. A process for preserving organic fibrous materials comprising treating said organic fibrous material with an effective preservative amount of an aqueous solution containing about 1% to about 4% of a composition including about 10% to about 35% by weight zinc acetate and about 50% to about 90% by weight of copper acetate based on the total metal acetate present.

10. The process as defined by claim 9, wherein said organic fibrous material is subjected to sea water and wherein said total metal acetate is present in said solution in a concentration of about 3 to 4% by weight of said solution.

11. A solution containing a preservative composition for wood comprising 65% to 90% copper acetate, 10% to 35% zinc acetate, and up to 10% boric acid, said solution containing up to 0.1% of an alkaline compound.

12. A process for preserving wood, comprising treating the wood with an aqueous solution of a preservative composition including 65% to 90% copper acetate, 10% to 35% zinc acetate, and up to 10% boric acid, wherein said preservative composition is present in said aqueous solution in an amount of from about 1% to about 4% and said aqueous solution contains up to 0.1% of an alkaline compound.

* * * * *